(12) United States Patent
Somanath et al.

(10) Patent No.: US 10,653,369 B2
(45) Date of Patent: May 19, 2020

(54) DEVICE FOR HEALTH MONITORING AND RESPONSE

(71) Applicant: Intel Corporation, Santa Clara, CA (US)

(72) Inventors: Gowri Somanath, Santa Clara, CA (US); Karthik Natarajan, Beaverton, OR (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 14/581,443

(22) Filed: Dec. 23, 2014

(65) Prior Publication Data

US 2016/0174913 A1 Jun. 23, 2016

(51) Int. Cl.
*A61B 5/00* (2006.01)
*A61B 5/11* (2006.01)
(Continued)

(52) U.S. Cl.
CPC ............ *A61B 5/747* (2013.01); *A61B 5/0022* (2013.01); *A61B 5/1117* (2013.01); *A61B 5/6804* (2013.01); *A61B 5/7282* (2013.01); *A61B 5/746* (2013.01); *G05B 1/01* (2013.01); *G06F 19/00* (2013.01); *G08B 21/0423* (2013.01); *G08B 21/0446* (2013.01); *G08B 21/0453* (2013.01); *G08B 25/08* (2013.01); *G16H 40/67* (2018.01);
(Continued)

(58) Field of Classification Search
USPC .................................................. 600/300–301
See application file for complete search history.

(56) References Cited

U.S. PATENT DOCUMENTS 5,544,649 A   8/1996   David et al.
8,864,663 B1  10/2014  Kahn et al.
(Continued)

FOREIGN PATENT DOCUMENTS

JP   H08234805 A   9/1996
JP   2004174168 A  6/2004
JP   2005177128 A  7/2005

OTHER PUBLICATIONS

International Search Report, PCT No. PCT/US2015/055108, dated Jan. 22, 2016, 4 pages.
(Continued)

*Primary Examiner* — Carl H Layno
*Assistant Examiner* — Dacheng Xie
(74) *Attorney, Agent, or Firm* — International IP Law Group, P.L.L.C.

(57) ABSTRACT

An apparatus, method, and machine-readable medium for health monitoring and response are described herein. The apparatus includes a processor and a number of sensors configured to collect data corresponding to a user of the device. The apparatus also includes a health monitoring and response application, at least partially including hardware logic. The hardware logic of the health monitoring and response application is to test the data collected by any of the sensors to match the collected data with a predetermined health condition, determine a current health condition of the user based on the predetermined health condition that matches the collected data, and automatically perform an action based on the current health condition of the user.

35 Claims, 6 Drawing Sheets

(51) Int. Cl.
*G05B 1/01* (2006.01)
*G08B 21/04* (2006.01)
*G08B 25/08* (2006.01)
*G06F 19/00* (2018.01)
*G16H 40/67* (2018.01)
*A61B 5/01* (2006.01)
*A61B 5/024* (2006.01)
*A61B 5/053* (2006.01)
*A61B 5/0404* (2006.01)

(52) U.S. Cl.
CPC ............ *A61B 5/01* (2013.01); *A61B 5/02438* (2013.01); *A61B 5/0404* (2013.01); *A61B 5/0533* (2013.01); *A61B 5/1118* (2013.01); *A61B 5/4094* (2013.01); *A61B 5/411* (2013.01); *A61B 5/6831* (2013.01); *A61B 5/7264* (2013.01); *A61B 2560/0252* (2013.01); *A61B 2562/0219* (2013.01); *G08B 21/0476* (2013.01)

(56) References Cited

U.S. PATENT DOCUMENTS

| | | |
|---|---|---|
| 2006/0074462 A1 | 4/2006 | Verhoef |
| 2009/0322513 A1 | 12/2009 | Hwang et al. |
| 2010/0286490 A1* | 11/2010 | Koverzin ............ G06F 19/3418 600/301 |
| 2012/0123218 A1* | 5/2012 | Renes ................ G06F 19/3418 600/300 |
| 2012/0139722 A1* | 6/2012 | Wong .................. A61B 5/0002 340/539.12 |
| 2012/0203076 A1 | 8/2012 | Fatta et al. |
| 2014/0163333 A1* | 6/2014 | Horseman ........... A61B 5/6887 600/301 |
| 2014/0288387 A1* | 9/2014 | Duplay ................ A61B 5/7275 600/301 |
| 2014/0306833 A1 | 10/2014 | Ricci |
| 2016/0278706 A1* | 9/2016 | Okamoto ........... G08B 21/0423 |

OTHER PUBLICATIONS

Perry, Mark et al.; "Multimodal and Ubiquitous Computing Systems: Supporting Independent-Living Older Users"; IEEE Transactions on Information Technology in Biomedicine, vol. 8 No. 3, Sep. 2004, 13 pages.

Supplemental European Search Report for European Patent Application No. EP 15873881 dated Jun. 18, 2018, 4 pages.

\* cited by examiner

300

400

DEVICE FOR HEALTH MONITORING AND RESPONSE

TECHNICAL FIELD

The present techniques relate generally to a device for health monitoring. More specifically, the present techniques relate to a device that is configured to sense particular health conditions and respond to such health conditions by performing a variety of actions.

BACKGROUND

There are many fitness (or health) related devices currently available on the market. Such devices are typically used to collect data relating to the physical activity of users. For example, such devices may collect data relating to the amount of calories a user burned or the distance a user traveled while walking or running. However, current devices do not take any action in response to the collection of such data. Instead, a user is typically presented with the data, and any action is left to the user's discretion based on the user's own target or goal. In other words, current fitness related devices are simple sense-and-log devices with limited functionality.

BRIEF DESCRIPTION OF THE DRAWINGS

The same numbers are used throughout the disclosure and the figures to reference like components and features. Numbers in the 100 series refer to features originally found in FIG. 1; numbers in the 200 series refer to features originally found in FIG. 2; and so on.

DESCRIPTION OF THE EMBODIMENTS

As discussed above, current fitness (or health) related devices are simple sense-and-log devices with limited functionality. Some current devices do provide data for remote monitoring by experts, such as, for example, a user's doctor or other care giver. However, because the number of users greatly exceeds the number of experts available to monitor such data, there are often high latencies in response. Therefore, this limited response is not sufficient.

Accordingly, embodiments described herein provide a sense-and-act device configured to detect particular health conditions or emergency situations, and respond in helpful ways in terms of environmental changes and notifications. For example, when the sense-and-act device detects a particular health condition or emergency situation, the device may automatically control the lights and locks within the user's home, call an emergency dispatch center, send data to other devices for remote monitoring, and/or upload data to a cloud server. In various embodiments, the sense-and-act device may be used as a geriatric emergency response instrument (GERI) to assist elderly users who may not be able to act on their own in emergency situations when the required latency is very low.

The sense-and-act device described herein may be implemented as a self-contained, wearable device including sensors and intelligent on-board algorithms to detect specific health conditions and automatically respond to such health conditions. For example, if sensor data indicates that the user has fallen or slipped, the sense-and-act device may respond by automatically unlocking the doors to the user's home and notifying emergency contacts. In parallel, the sense-and-act device may save and upload the sensor data to a cloud server or other computing devices for remote monitoring by medical experts or the user's family members or friends. Moreover, the sense-and-act device may tailor its response to the specific health condition that was detected. For example, the sense-and-act device may automatically turn on the air conditioner and/or fans if it determines that the user is having a heat stroke, or automatically turn on the lights if it determines that the user is sleepwalking.

Figure 1:
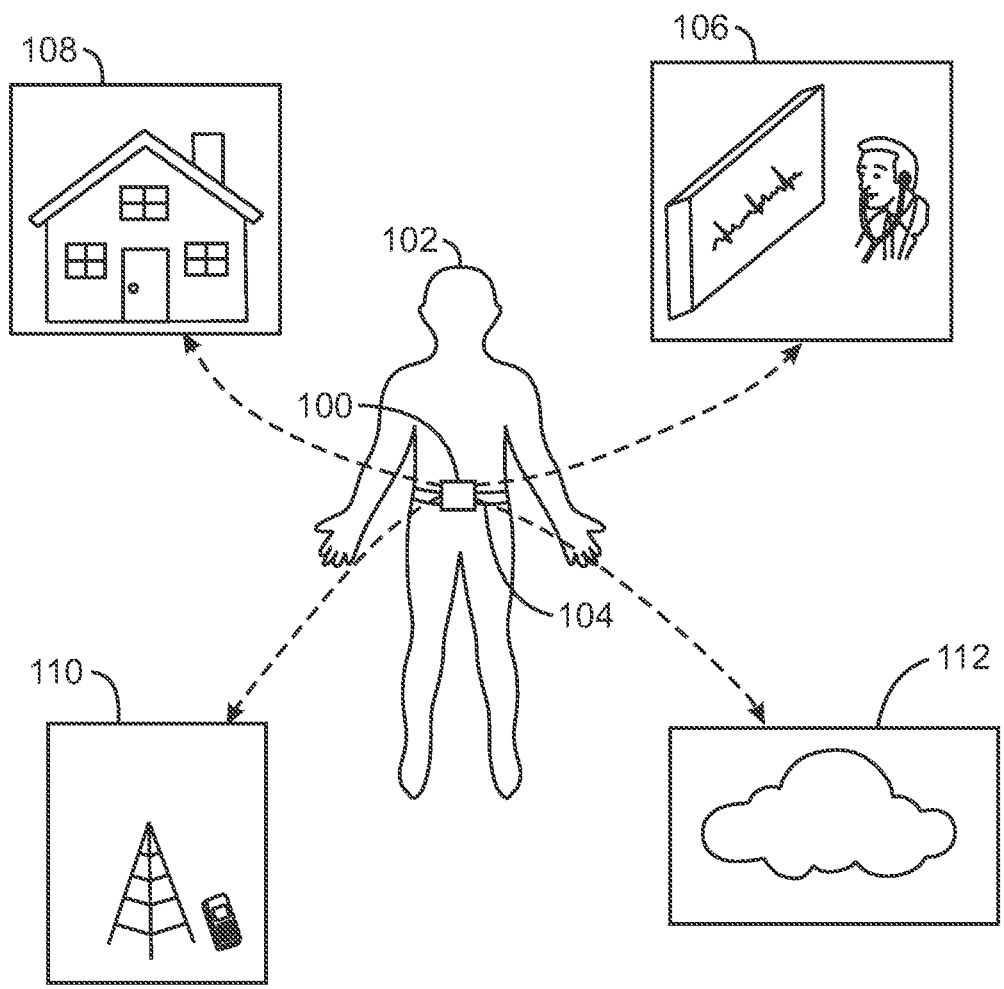
FIG. 1 is a schematic according to one embodiment illustrating the functionality of a sense-and-act device that can be used to monitor health conditions corresponding to a user.

FIG. 1 is a schematic according to one embodiment illustrating the functionality of a sense-and-act device 100 that can be used to monitor health conditions corresponding to a user 102. According to embodiments described herein, the sense-and-act device 100 may be an apparatus such as a wearable computing device including a processing unit, Wi-Fi™ and/or Bluetooth® connectivity, and a number of different sensors. For example, the sense-and-act device 100v may include a heart rate sensor, an accelerometer, a gyroscope, a thermal sensor, a galvanic skin response (GSR) sensor, and an electrocardiogram (ECG) sensor, or any combinations thereof. In some embodiments, the sense-and-act device 100 may include an apparatus in the environment of the user, such as a camera, a motion sensing camera, an infrared sensor, and the like. Further, the sense-and-act device 100 may include any number of additional health-related sensors, depending on the details of the particular implementation. The sense-and-act device 100 may also include one or more applications or modules for processing sensor data relating to the user's health, determining appropriate responses for any detected health conditions or emergency situations, and automatically effectuating such responses.

In various embodiments, the sense-and-act device 100 may prompt the user 102 to complete a general set up procedure prior to first use. For example, the sense-and-act device 100 may prompt the user 102 to enter general information relating to the user's health, such as, for example, the user's current weight and blood pressure, as well as specific information relating to any current or previous health conditions. The sense-and-act device 100 may also prompt the user 102 to enter phone numbers for the user's desired emergency contact, as well as the user's doctor and/or other care giver. In addition, the sense-and-act device 100 may prompt the user 102 to set up an online account for storing data on the cloud server. Further, if the user's home is not already a "smart home," the sense-and-act device 100 may instruct the user 102 to install controllable lights, locks, fans, etc., in the home.

In the embodiment shown in FIG. 1, the sense-and-act device 100 is enclosed in a belt 104 worn around the user's waist. However, in other embodiments, the sense-and-act device 100 may be enclosed in a watch or bracelet worn around the user's wrist, or enclosed in an anklet worn around the user's ankle, for example. In other embodiments, the sense-and-act device 100 may be directly attached to the user's skin or embedded in the user's skin. Moreover, it is to be understood that the sense-and-act device 100 may be worn by the user 102 in any manner as long as the sensors are able to collect data corresponding to the user 100.

The schematic of FIG. 1 illustrates a number of different responses that may be effectuated by the sense-and-act device 100, depending on the detected health condition or emergency situation. As illustrated by block 106, in some embodiments, the sense-and-act device 100 may send data to remote computing devices to inform others about the situation. For example, if the user 102 is experiencing a heart attack or seizure, the sense-and-act device 100 may automatically send data corresponding to the health condition to the user's doctor.

Although shown as attached to a user in this example, as noted herein, the sense-and-act device 100 may be present in a user's 102 environment, but not worn by the user 102. For example, the device may be a time-of-flight (TOF) motion camera that is used to capture position, motion, heart rate, gait, and the like. In this example, the sense-and-act device 100 may compare current information on the patient to previous information, such as to identify changes in gait that may indicate a stroke, to sense heart rate, and the like.

As illustrated by block 108, in some embodiments, the sense-and-act device 100 is communicably coupled to the user's smart home via Wi-Fi™ or Bluetooth®, for example. In such embodiments, the sense-and-act device 100 may be configured to automatically control different features of the user's home, such as the lights, locks, fans, air conditioning unit, or windows. This may allow the sense-and-act device 100 to adjust the conditions within the user's home based on any detected health condition or emergency situation. For example, if the sense-and-act device 100 determines that the user 102 has fallen or slipped, the sense-and-act device 100 may automatically unlock the doors to the user's home to allow emergency responders to enter. In addition, in some embodiments, the sense-and-act device 100 may be similarly linked to the user's vehicle, and may be configured to automatically control various features of the user's vehicle in the event of an emergency.

As illustrated by block 110, the sense-and-act device 100 may be configured to automatically call an emergency dispatch center in response to any detected health condition or emergency situation. In some embodiments, the sense-and-act device 100 may also be configured to automatically call any number of preset emergency contacts, such as a family member or a close neighbor.

Further, as illustrated by block 112, the sense-and-act device 100 may automatically upload sensor data and information corresponding to the user's previous health conditions or emergency situations to a cloud server. In some embodiments, this may allow the user 102, or the user's care giver, to build an online health portfolio that may be shared with doctors or other care givers in the future. In addition, in some embodiments, this may allow others, such as the user's doctors, care givers, or family, to stream live data corresponding to the user's health from a remote location. As an example, if the user is an elderly man, the user's daughter may be able to monitor her father's health while at work.

Figure 2:
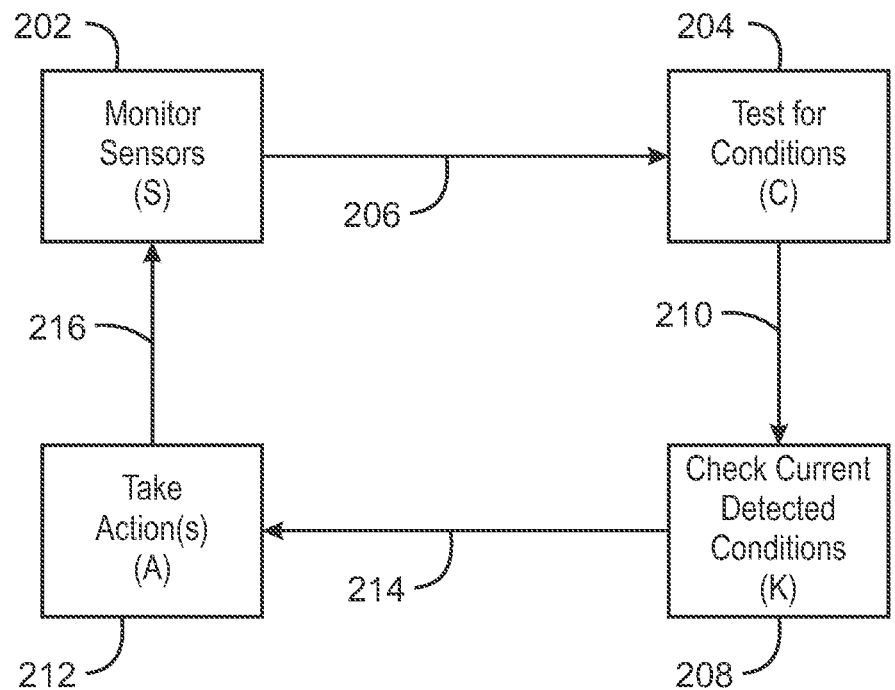
FIG. 2 is a state diagram according to one embodiment showing a method for sensing and responding to particular health conditions using the sense-and-act device described herein.

FIG. 2 is a state diagram 200 according to one embodiment showing a method 200 for sensing and responding to particular health conditions using the sense-and-act device described herein. Beginning at block 202, the sense-and-act device may monitor a given set of sensors (S) for a predetermined set of health conditions (C). The set of sensors may include, but is not limited to, S={heart rate, accelerometer, temperature, override-button, TOF camera}. The predetermined set of health conditions may include C={normal, active/moving, fall, heart rate conditions, fever}. However, it is to be understood that the sense-and-act device described herein may be used to monitor any type of health condition for any user. For example, the sense-and-act device may also be used to monitor for severe allergic reactions, seizures, or abnormal blood sugar levels.

The method 200 may then flow from block 202 to block 204, as indicated by arrow 206. At bock 204, the sense-and-act device may test for any of the health conditions in the predetermined set of health conditions using a variety of different algorithms. For example, the sense-and-act device may test for particular health conditions using the accelerometer based algorithm, heart rate sensor algorithm, or temperature sensor algorithm described below. Further, it is to be understood that the sense-and-act device may use any number of additional algorithms not described herein to test for particular health conditions.

The method 200 may then flow from block 204 to block 208, as indicated by arrow 210. At block 208, the sense-and-act device may detect any number of current health conditions (K) based on the testing performed at block 204. The current health condition (K) of the user may be a subset of the predetermined set of health conditions (C), K ⊂ C. The method may then flow from block 208 to block 212, as indicated by arrow 214. At block 212, the sense-and-act device may determine one or more actions to perform based on the current health conditions detected at block 208. The one or more actions may be chosen from a predetermined set of actions (A). The predetermined set of actions (A) may include, but is not limited to, A={upload condition, wait-for-override-button, upload data, email+call emergency contact, turn on home light, unlock door}. The sense-and-act device may then automatically perform such action. The method 200 may then flow from block 212 back to block 202, as indicated by arrow 216.

As discussed above, various different algorithms may be used to test sensor data to determine whether the user's current health condition (K) matches any of the predetermined set of health conditions (C). For example, in various embodiments, the user's current health condition (K) may be populated using the following algorithms. At initialization, K={normal}; all counters are set to 0; and all flags are set to false. Various thresholds, such as $\Delta t$, $\tau$, and $\sigma$, are scalar values set based on the particular sensor being monitored.

For an accelerometer based algorithm, the accelerometer may be calibrated to estimate the offset and scale values to convert ADC read voltage to G-force. Let of $f_i$ and $g_i$ denote the offset and scale values along the corresponding axis i, where i∈N {x, y, z axes}. The main intuition behind fall detection is that a fall is a sudden peak in acceleration, followed by a period of "no-activity." As an example, the following algorithm can be used to detect a fall using simple threshold on acceleration. It can be understood that the pseudo code shown below and in further example, is merely one embodiment of the techniques, and any number of other implementations may be used.

1. At every $\Delta t_a$ time interval, read the sensor values $a_i$ respectively.
2. Let $\alpha$, $\beta$ denote the current and previously known total accelerations. Calculate total acceleration as sum of accelerations along each axis as $$\alpha = \sum_{i \in N} \left( \frac{a_i - \text{off}_i}{g_i} \right)^2.$$

3. If $\alpha > \sigma_0$ AND $\alpha < \sigma_1$ set K = K ∪ active – moving.
4. If acceleration exceeds threshold, i.e., $\alpha > \sigma_1$, then set flag $\text{FALL}_{SUSPECTED}$=TRUE.
5. If $\text{FALL}_{SUSPECTED}$==TRUE
   a. If abs($\alpha$-$\beta$) < $\sigma_2$, then $\text{counter}_{pf}$ = $\text{counter}_{pf}$ + 1. Else $\text{counter}_{nf}$ = $\text{counter}_{nf}$ + 1.
   b. If ($\text{couter}_{pf} > \sigma_3$ AND $\text{counter}_{nf} < \sigma_4$) then set $\text{FALL}_{DETECTED}$ = TRUE, $\text{counter}_{pf}$ = 0.
   c. If $\text{counter}_{nf} > \sigma_5$ then set $\text{FALL}_{SUSPECTED}$ = FALSE, $\text{counter}_{pf}$ = 0, $\text{counter}_{nf}$ = 0.
6. If $\text{FALL}_{DETECTED}$ == TRUE then set K = K ∪ FALL.

For a heart rate sensor algorithm, an IR based pulse sensor may be used. The pulse rate may be calculated as beats per minute, measured as the time between peaks in sensor measurement. Due to noise and motion, the following algorithm may be used to estimate a robust pulse rate.

1. Let t denote the current system time in milliseconds. Let $\text{heart}_{current}$ and $\text{heart}_{prev}$ denote the last two measured heart rate in beats per minute.
2. At every $\Delta t_p$ monitor the input sensor value $p_t$.
3. If $p_t < \tau_1$ then
   Set flags $\text{PULSE}_{down}$ = TRUE, $\text{PULSE}_{up}$ = FALSE. Set counters $\text{counter}_{down}$ = $\text{counter}_{down}$ + 1, $\text{counter}_{up}$ = 0.
4. If ($\text{PULSE}_{down}$ == TRUE and $\text{counter}_{down} < \tau_2$ and $p_t > \tau_3$) then it's a noise spike, hence set $\text{PULSE}_{down}$ = FALSE, $\text{counter}_{down}$ = 0, $\text{counter}_{up}$ = 0.
5. If ($\text{counter}_{pulse} < \text{MAX}_{pulse}$ and $\text{PULSE}_{down}$ == TRUE and $\text{counter}_{down} > \tau_4$ and $p_t > \tau_5$) then set
   $\text{PULSE}_{up}$ = true , $\text{PULSE}_{down}$ = false
   $\text{counter}_{pulse}$ = $\text{counter}_{pulse}$ + 1
   $\text{pulse}_{time}[\text{counter}_{pulse}]$ = t
6. If $\text{counter}_{pulse} \geq \text{MAX}_{pulse}$ then calculate pulse rate as follows:
   a. Calculate mean time between pulse crests as:
      For i = 1:$\text{counter}_{pulse}$-1
      $\text{sum}_{dp}$ = $\text{sum}_{dp}$ + ($\text{pulse}_{time}$ [i + 1] – $\text{pulse}_{time}$[i])
      End For
      $\text{mean}_{dp}$ = $\text{sum}_{dp}$/$\text{counter}_{pulse}$
   b. Eliminate noisy measurements using the mean
      For i = 1:$\text{counter}_{pulse}$-1
      dp = ($\text{pulse}_{time}$ [i + 1] – $\text{pulse}_{time}$[i])
      if dp < $\tau_6$ * $\text{mean}_{dp}$ and dp > $\tau_7$ * $\text{mean}_{dp}$ then
      $\text{clean}_{dp}$ = $\text{clean}_{dp}$ + dp, $\text{counter}_{clean}$ = $\text{counter}_{clean}$ + 1
      End For
   c. $\text{mean}_{cleandp}$ = $\text{clean}_{dp}$/$\text{counter}_{clean}$
   d. Calculate beats per minute as 6000/mean_cleandp.
7. Set $\text{heart}_{current}$ and $\text{heart}_{prev}$ accordingly.
8. Update the record of monthly average and historic max of recorded bpm at this time of day.
9. If any one or more of the following conditions hold, set K = K ∪ heart rate conditions:
   $\text{heart}_{current} > \tau_8$
   $\text{heart}_{current} < \tau_9$
   abs($\text{heart}_{current}$ – $\text{heart}_{prev}$) > $\tau_{10}$ For a temperature sensor algorithm, a digital or analog sensor may be monitored at regular intervals to determine the user's body temperature. If the user's body temperature exceeds a threshold $\tau_{11}$, the sense-and-act device may set K=K∪fever.

In some embodiments, the sense-and-act device may perform particular actions at regular time intervals regardless of the user's current health conditions. For example, at regular time interval $\Delta t$, the sense-and-act device may upload the user's current health condition to the cloud server. The cloud server may be accessible through a regulated web interface (or mobile application interface). For example, the data in K, $\text{heart}_{current}$ may be uploaded to the cloud server and then represented graphically or textually on the web interface.

Figure 3:
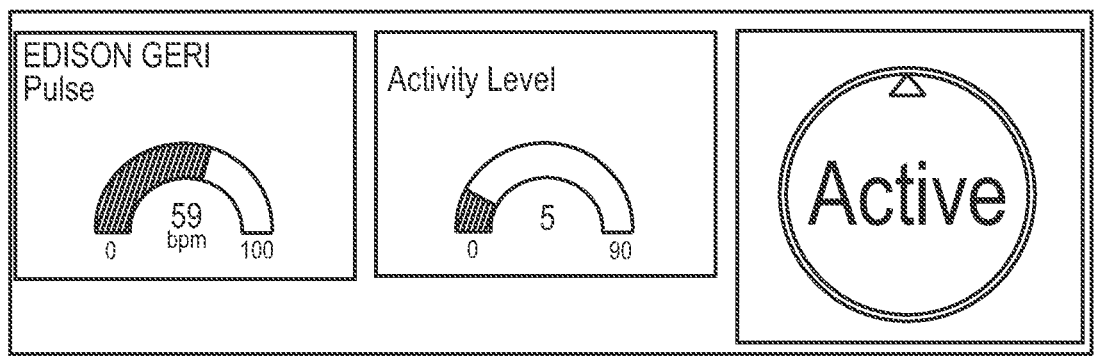
FIG. 3 is a schematic according to one embodiment showing a web interface displaying data obtained by the sense-and-act device described herein.

FIG. 3 is a schematic according to one embodiment showing a web interface 300 displaying data obtained by the sense-and-act device described herein. Specifically, the web interface 300 shown in FIG. 3 displays data relating to the user's pulse and activity level. This data may be used to detect a number of health conditions, such as whether the user is currently active or has fallen and is unable to get up.

Figure 4:
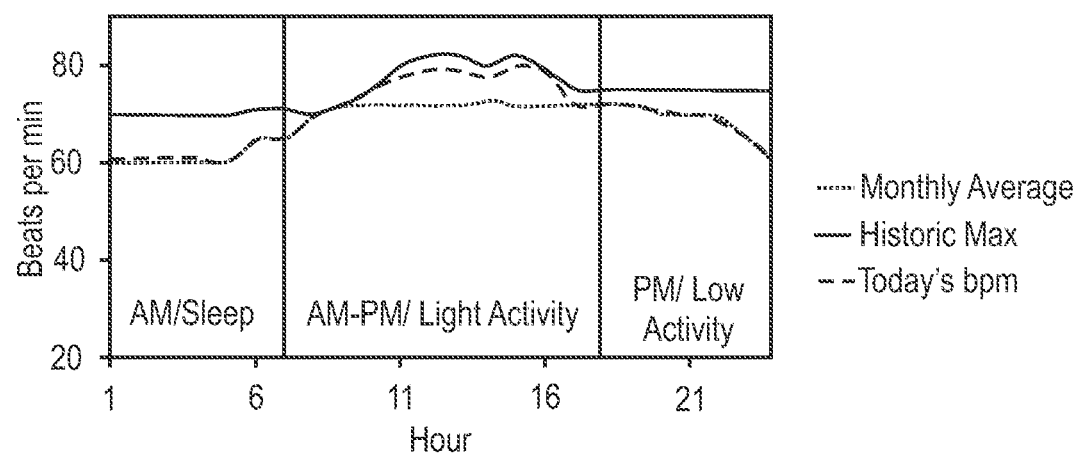
FIG. 4 is a schematic according to another embodiment showing a web interface displaying data obtained by the sense-and-act device described herein.

FIG. 4 is a schematic according to another embodiment showing a web interface 400 displaying data obtained by the sense-and-act device described herein. Specifically, the web interface 400 shown in FIG. 4 displays data relating to the user's heart rate, measured in beats per minute (bpm). This data may be used to compare the user's current heart rate to the user's heart rate in the past, such as the user's monthly average or historic maximum heart rate.

In some embodiments, if the sense-and-act device determines that the user has fallen and has an abnormal heart rate, i.e., {FALL, heart rate conditions} ⊂ K, the sense-and-act device may respond by turning on the lights in the user's home. The sense-and-act device may simultaneously raise an alarm and wait for the user to activate the override-button. If the user does not activate the override button within a certain time period, the sense-and-act device may automatically email or call the user's emergency contacts, start uploading data to the cloud server, and allow emergency contacts to view the data through a web interface.

In some embodiments, the sense-and-act device may be configured to adjust its settings based on feedback received from others, such as the user's doctor or other care giver, via the web interface. For example, the user's doctor may indicate which information he wants to view via the web interface, and the sense-and-act device may only upload the requested information. In addition, the user's doctor may request that specific alerts be sent straight to his own mobile device or personal computer in the case of an emergency, such as if the user is having a heart attack or stroke.

Further, in some embodiments, the sense-and-act device described herein may be used to gather data corresponding to the user's fitness. For example, the sense-and-act device may track the user's location to determine distance walked, and may then determine information such as the amount of calories burned or number of steps walked based on the user's personal information. In addition, the sense-and-act device may include applications or modules that allow the user to perform various health related functions, such as keeping a fitness diary to track the user's exercise or calories consumed each day. If the user has a particular ongoing health condition, the user may also download applications relating to that health condition. For example, if the user has chronic hypertension, the user may download an application that is configured to record the user's blood pressure on a daily basis or provide the user with helpful tips for managing his condition.

Figure 5:
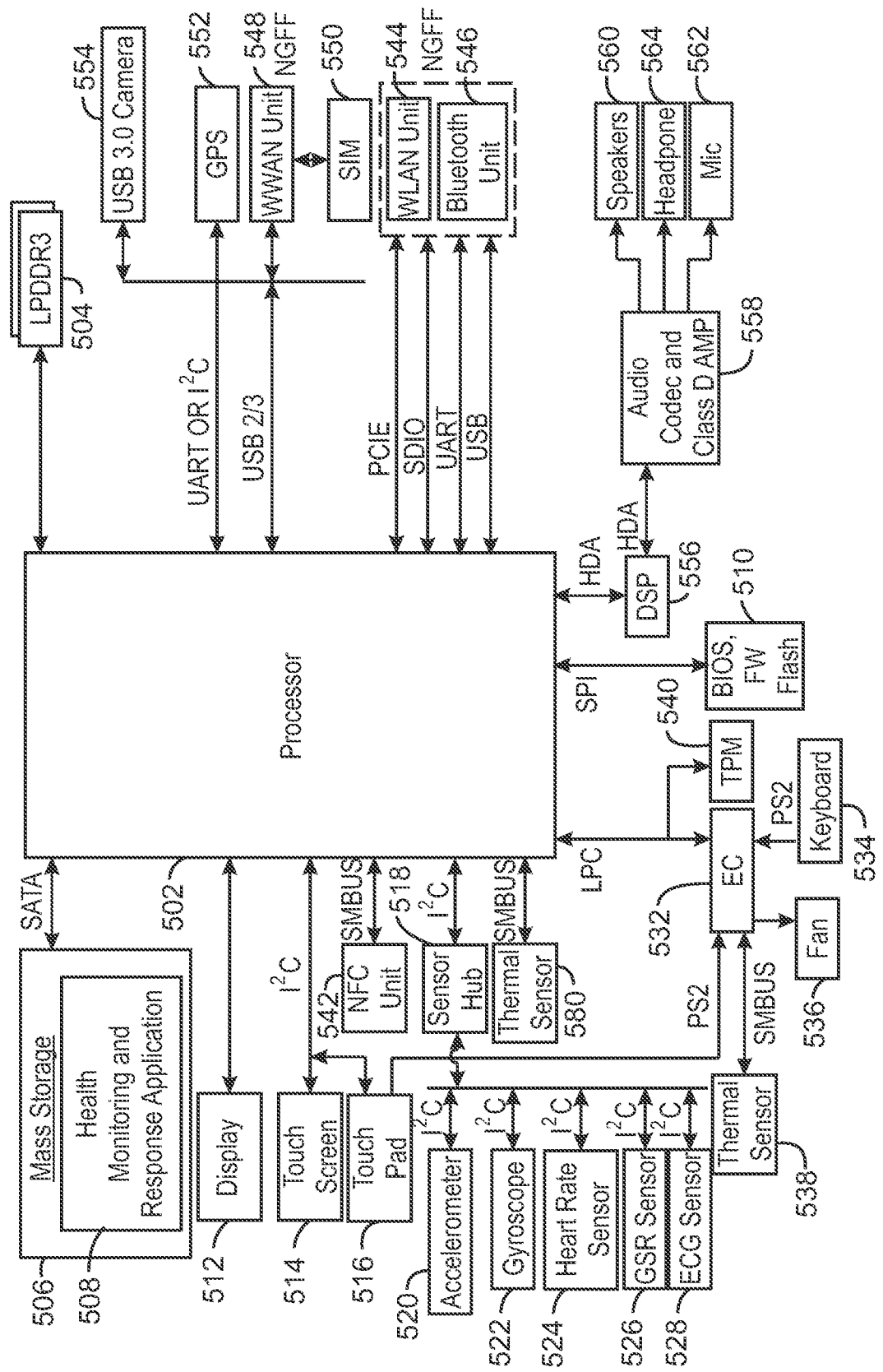
FIG. 5 is a block diagram of a computing device configured to sense and respond to particular health conditions according to embodiments described herein.

FIG. 5 is a block diagram of a computing device 500 configured to sense and respond to particular health conditions according to embodiments described herein. The computing device 500 shown in FIG. 5 may include any combination of components. These components may be implemented as ICs, portions thereof, discrete electronic devices, or other modules, logic, hardware, software, firmware, or a combination thereof adapted in a computing device, or as components otherwise incorporated within a chassis of the computing device 500. Note also that the block diagram of FIG. 5 is intended to show a high level view of many components of the computing device. However, it is to be understood that some of the components shown may be omitted, additional components may be present, and different arrangements of the components shown may occur in other implementations. As a result, the techniques described above may be implemented in any portion of one or more of the interconnects illustrated or described below.

As shown in FIG. 5, a processor 502, in one embodiment, includes a microprocessor, multi-core processor, multi-threaded processor, an ultra-low voltage processor, an embedded processor, or other known processing element. In the illustrated implementation, processor 502 acts as a main processing unit and central hub for communication with many of the various components of the computing device 500. As one example, processor 502 is implemented as a system on a chip (SoC). As a specific illustrative example, processor 502 includes an Intel® Architecture Core™-based processor such as an i3, i5, i7 or another such processor available from Intel Corporation, Santa Clara, Calif. However, understand that other low power processors such as available from Advanced Micro Devices, Inc. (AMD) of Sunnyvale, Calif., a MIPS-based design from MIPS Technologies, Inc. of Sunnyvale, Calif., an ARM-based design licensed from ARM Holdings, Ltd. or customer thereof, or their licensees or adopters may instead be present in other embodiments such as an Apple A5/A6 processor, a Qualcomm Snapdragon processor, or TI OMAP processor. Note that many of the customer versions of such processors are modified and varied; however, they may support or recognize a specific instructions set that performs defined algorithms as set forth by the processor licensor. Here, the microarchitectural implementation may vary, but the architectural function of the processor is usually consistent. Certain details regarding the architecture and operation of processor 502 in one implementation will be discussed further below to provide an illustrative example.

Processor 502, in one embodiment, communicates with a system memory 504. In some embodiments, the system memory 504 can be implemented via multiple memory devices to provide for a given amount of system memory. As examples, the system memory 504 can be in accordance with a Joint Electron Devices Engineering Council (JEDEC) low power double data rate (LPDDR)-based design such as the current LPDDR2 standard according to JEDEC JESD 209-2E (published April 2009), or a next generation LPDDR standard to be referred to as LPDDR3 or LPDDR4 that will offer extensions to LPDDR2 to increase bandwidth. In various implementations, the individual memory devices may be of different package types, such as single die package (SDP), dual die package (DDP) or quad die package (Q17P). These devices, in some embodiments, are directly soldered onto a motherboard to provide a lower profile solution, while in other embodiments the devices are configured as one or more memory modules that in turn couple to the motherboard by a given connector. And of course, other memory implementations are possible such as other types of memory modules, e.g., dual inline memory modules (DIMMs) of different varieties including but not limited to microDIMMs, MiniDIMMs. In a particular illustrative embodiment, memory is sized between 2 GB and 16 GB, and may be configured as a DDR3LM package or an LPDDR2 or LPDDR3 memory that is soldered onto a motherboard via a ball grid array (BGA).

To provide for persistent storage of information such as data, applications, one or more operating systems, and so forth, a mass storage 506 may also couple to processor 502. In various embodiments, to enable a thinner and lighter system design as well as to improve system responsiveness, this mass storage 506 may be implemented via a solid state drive (SSD). However in other embodiments, the mass storage 506 may primarily be implemented using a hard disk drive (HDD) with a smaller amount of SSD storage to act as a SSD cache to enable non-volatile storage of context state and other such information during power down events so that a fast power up can occur on re-initiation of system activities.

In various embodiments, the mass storage 506 includes a health monitoring and response application 508 that is configured to run on the computing device 500. The health monitoring and response application 508 may include instructions for sensing and responding to health conditions corresponding to a user of the computing device 500. Further, in some embodiments, the health monitoring and response application 508 encompasses a number of different applications for performing various tasks, such as analyzing sensor data, testing for certain health conditions, and taking particular actions depending on the detected health conditions.

Also shown in FIG. 5, a flash device 510 may be coupled to processor 502, e.g., via a serial peripheral interface (SPI). This flash device 510 may provide for non-volatile storage of system software, including a basic input/output software (BIOS) as well as other firmware of the system.

In various embodiments, the mass storage 506 is implemented by a SSD alone or as a disk, optical or other drive with an SSD cache. In some embodiments, the mass storage 506 is implemented as a SSD or as a HDD along with a restore (RST) cache module. In various implementations, the HDD provides for storage of between 320 GB-4 terabytes (TB) and upward while the RST cache is implemented with a SSD having a capacity of 24 GB-256 GB. Note that such SSD cache may be configured as a single level cache (SLC) or multi-level cache (MLC) option to provide an appropriate level of responsiveness. In a SSD-only option, the module may be accommodated in various locations such as in a mSATA or NGFF slot. As an example, an SSD has a capacity ranging from 120 GB-1 TB.

Various input/output (IO) devices may be present within the computing device 500. Specifically shown in the embodiment of FIG. 5 is a display 512, which may be a high definition LCD or LED panel configured within a lid portion of the chassis. This display panel may also provide for a touch screen 514, e.g., adapted externally over the display panel such that via a user's interaction with this touch screen, user inputs can be provided to the system to enable desired operations, e.g., with regard to the display of information, accessing of information and so forth. In one embodiment, the display 512 may be coupled to the processor 502 via a display interconnect that can be implemented as a high performance graphics interconnect. The touch screen 514 may be coupled to the processor 502 via another interconnect, which in an embodiment can be an $I^2C$ interconnect. As further shown in FIG. 5, in addition to the touch screen 514, user input by way of touch can also occur via a touch pad 516, which may be configured within the chassis and may also be coupled to the same $I^2C$ interconnect as the touch screen 514.

The display panel may operate in multiple modes. In a first mode, the display panel can be arranged in a transparent state in which the display panel is transparent to visible light. In various embodiments, the majority of the display panel may be a display except for a bezel around the periphery.

When the computing device 500 is operated in a notebook mode and the display panel is operated in a transparent state, a user may view information that is presented on the display panel while also being able to view objects behind the display. In addition, information displayed on the display panel may be viewed by a user positioned behind the display. Further, the operating state of the display panel can be an opaque state in which visible light does not transmit through the display panel.

In a tablet mode, the computing device 500 is folded shut such that the back display surface of the display panel comes to rest in a position such that it faces outwardly towards a user, when the bottom surface of the base panel is rested on a surface or held by the user. In the tablet mode of operation, the back display surface performs the role of a display and user interface, as this surface may have touch screen functionality and may perform other known functions of a conventional touch screen device, such as a tablet device. To this end, the display panel may include a transparency-adjusting layer that is disposed between a touch screen layer and a front display surface. In some embodiments, the transparency-adjusting layer may be an electrochromic layer (EC), a LCD layer, or a combination of EC and LCD layers.

In various embodiments, the display can be of different sizes, e.g., an 11.6" or a 13.3" screen, and may have a 16:9 aspect ratio, and at least 300 nits brightness. Also the display may be of full high definition (HD) resolution (at least 1920×1080 p), be compatible with an embedded display port (eDP), and be a low power panel with panel self-refresh.

As to touch screen capabilities, the computing device 500 may provide for a display multi-touch panel that is multi-touch capacitive and being at least 5 finger capable. And in some embodiments, the display may be 10 finger capable. In one embodiment, the touch screen is accommodated within a damage and scratch-resistant glass and coating (e.g., Gorilla Glass™ or Gorilla Glass 2™) for low friction to reduce "finger burn" and avoid "finger skipping". To provide for an enhanced touch experience and responsiveness, the touch panel, in some implementations, has multi-touch functionality, such as less than 2 frames (30 Hz) per static view during pinch zoom, and single-touch functionality of less than 1 cm per frame (30 Hz) with 200 ms (lag on finger to pointer). The display, in some implementations, supports edge-to-edge glass with a minimal screen bezel that is also flush with the panel surface, and limited 10 interference when using multi-touch.

According to embodiments described herein, various sensors are present within the computing device 500 and may be coupled to the processor 502 in different manners. Specifically, certain inertial and environmental sensors may be coupled to the processor 502 through a sensor hub 518, e.g., via an I²C interconnect. These sensors may include an accelerometer 520, a gyroscope 522, a heart rate sensor 524, a GSR sensor 526, and an ECG sensor 528. Other environmental sensors may include one or more thermal sensors 530, which in some embodiments couple to the processor 502 via a system management bus (SMBus) bus. The computing device 500 may also include any number of additional sensors not shown in FIG. 5, such as an ambient light sensor (ALS) and a compass, for example.

Many different use cases can be realized using the various inertial and environmental sensors present in the platform. Specifically, according to embodiments described herein, the sensors may be used to obtain data corresponding to the health of the user. The computing device 500 may use such data to detect particular health conditions, and then take appropriate action in response to any detected health conditions. Further, in some embodiments, the sensors may also be used to enable advanced computing operations including perceptual computing and also allow for enhancements with regard to power management/battery life, security, and system responsiveness.

For example with regard to power management/battery life issues, based at least on part on information from an ambient light sensor, the ambient light conditions in a location of the platform may be determined, and the intensity of the display may be controlled accordingly. Thus, power consumed in operating the display is reduced in certain light conditions.

As to security operations, based on context information obtained from the sensors, such as location information, it may be determined whether a user is allowed to access certain secure documents. For example, a user may be permitted to access such documents at a work place or a home location. However, the user may be prevented from accessing such documents when the platform is present at a public location. This determination, in one embodiment, is based on location information, e.g., determined via a GPS sensor or camera recognition of landmarks. Other security operations may include providing for pairing of devices within a close range of each other, e.g., the computing device 500 described herein and the user's smart home or smartphone. Certain sharing, in some implementations, are realized via near field communication when these devices are so paired. However, when the devices exceed a certain range, such sharing may be disabled. Furthermore, when pairing a platform as described herein and a smartphone, an alarm may be configured to be triggered when the devices move more than a predetermined distance from each other, when in a public location. In contrast, when these paired devices are in a safe location, e.g., a work place or home location, the devices may exceed this predetermined limit without triggering such alarm.

Responsiveness may also be enhanced using the sensor information. For example, even when a platform is in a low power state, the sensors may still be enabled to run at a relatively low frequency. Accordingly, any changes in a location of the platform, e.g., as determined by inertial sensors or a GPS sensor, may be determined. If no such changes have been registered, a faster connection to a previous wireless hub such as a Wi-Fi™ access point or similar wireless enabler occurs, as there is no need to scan for available wireless network resources in this case. Thus, a greater level of responsiveness when waking from a low power state is achieved.

It is to be understood that many other use cases may be enabled using sensor information obtained via the integrated sensors within a platform as described herein, and the above examples are only for purposes of illustration. Using a system as described herein, a perceptual computing device may allow for the addition of alternative input modalities, including gesture recognition, and enable the computing device 500 to sense user operations and intent.

In various embodiments, the accelerometer 520 may be a 3-axis accelerometer having data rates of at least 50 Hz, and the gyroscope 522 may be a 3-axis gyroscope. In addition, an e-compass/magnetometer may be present. Also, one or more proximity sensors may be provided (e.g., to sense when a user is in proximity (or not) to the computing device 500 and adjust power/performance to extend battery life). For some OS's Sensor Fusion capability including the accelerometer, gyroscope, and compass may provide enhanced features. In addition, via a sensor hub having a real-time clock (RTC), a wake from sensors mechanism may be realized to receive sensor input when a remainder of the computing device 500 is in a low power state. Other sensors can include ACPI sensors for internal processor, memory, and skin temperature monitoring to enable changes to processor and system operating states based on sensed parameters.

In an embodiment, the OS may be a Microsoft® Windows® 8 OS that implements Connected Standby (also referred to herein as Win8 CS). Windows 8 Connected Standby or another OS having a similar state can provide, via a platform as described herein, very low ultra idle power to enable applications to remain connected, e.g., to a cloud-based location, at very low power consumption. The platform can supports 3 power states, namely screen on (normal); Connected Standby (as a default "off" state); and shutdown (zero watts of power consumption). Thus in the Connected Standby state, the platform is logically on (at minimal power levels) even though the screen is off. In such a platform, power management can be made to be transparent to applications and maintain constant connectivity, in part due to offload technology to enable the lowest powered component to perform an operation.

Also shown in FIG. 5, various peripheral devices may be coupled to the processor 502 via a low pin count (LPC) interconnect. In the embodiment shown, various components can be coupled through an embedded controller (EC) 532. Such components can include a keyboard 534 (e.g., coupled via a PS2 interface), a fan 536, and a thermal sensor 538. In some embodiments, the touch pad 516 may also be coupled to the EC 532 via a PS2 interface. In addition, a security processor, such as a trusted platform module (TPM) 540 in accordance with the Trusted Computing Group (TCG) TPM Specification Version 1.2, dated Oct. 2, 2003, may also be coupled to the processor 502 via this LPC interconnect. However, it is to be understood that the scope of the present techniques is not limited in this regard and secure processing and storage of secure information may be in another protected location such as a static random access memory (SRAM) in a security coprocessor, or as encrypted data blobs that are only decrypted when protected by a secure enclave (SE) processor mode.

In a particular implementation, peripheral ports may include a high definition media interface (HDMI) connector (which can be of different form factors such as full size, mini or micro); one or more USB ports, such as full-size external ports in accordance with the Universal Serial Bus Revision 3.0 Specification (November 2008), with at least one powered for charging of USB devices (such as smartphones) when the computing device 500 is in Connected Standby state and is plugged into AC wall power. In addition, one or more Thunderbolt™ ports can be provided. Other ports may include an externally accessible card reader such as a full size SD-XC card reader or a SIM card reader for WWAN (e.g., an 8 pin card reader). For audio, a 3.5 mm jack with stereo sound and microphone capability (e.g., combination functionality) can be present, with support for jack detection (e.g., headphone only support using microphone in the lid or headphone with microphone in cable). In some embodiments, this jack can be re-taskable between stereo headphone and stereo microphone input. Also, a power jack can be provided for coupling to an AC brick.

The computing device 500 can communicate with external devices in a variety of manners, including wirelessly. In the embodiment shown in FIG. 5, various wireless modules, each of which can correspond to a radio configured for a particular wireless communication protocol, are present. One manner for wireless communication in a short range such as a near field may be via a near field communication (NFC) unit 542 which may communicate, in one embodiment with the processor 502 via an SMBus. Note that, via this NFC unit 542, devices in close proximity to each other can communicate. For example, a user can enable the computing device 500 to communicate with another (e.g.,) portable device, such as the user's smart home or smartphone, via adapting the two devices together in close relation and enabling the transfer of information. Wireless power transfer may also be performed using an NFC system.

Using the NFC unit 542 described herein, users can bump devices side-to-side and place devices side-by-side for near field coupling functions (such as near field communication and wireless power transfer (WPT)) by leveraging the coupling between coils of one or more of such devices. More specifically, embodiments provide devices with strategically shaped, and placed, ferrite materials, to provide for better coupling of the coils. Each coil has an inductance associated with it, which can be chosen in conjunction with the resistive, capacitive, and other features of the computing device 500 to enable a common resonant frequency for the computing device 500.

As further shown in FIG. 5, additional wireless units can include other short range wireless engines including a WLAN unit 544 and a Bluetooth® unit 546. Using the WLAN unit 544, Wi-Fi™ communications in accordance with a given Institute of Electrical and Electronics Engineers (IEEE) 802.11 standard can be realized, while via the Bluetooth® unit 546, short range communications via a Bluetooth® protocol can occur. These units may communicate with the processor 502 via, e.g., a USB link or a universal asynchronous receiver transmitter (UART) link. Alternatively, these units may couple to the processor 502 via an interconnect according to a Peripheral Component Interconnect Express™ (PCIe™) protocol, e.g., in accordance with the PCI Express™ Specification Base Specification version 3.0 (published Jan. 17, 2007), or another such protocol such as a serial data input/output (SDIO) standard. Of course, the actual physical connection between these peripheral devices, which may be configured on one or more add-in cards, can be by way of the NGFF connectors adapted to a motherboard.

In addition, wireless wide area communications, e.g., according to a cellular or other wireless wide area protocol, can occur via a WWAN unit 548, which in turn may couple to a subscriber identity module (SIM) 550. In addition, to enable receipt and use of location information, a GPS module 552 may also be present. Note that in the embodiment shown in FIG. 5, the WWAN unit 548 and an integrated capture device, such as a camera module 554, may communicate via a given USB protocol such as a USB 2.0 or 3.0 link, or a UART or I²C protocol. Again the actual physical connection of these units can be via adaptation of a NGFF add-in card to an NGFF connector configured on the motherboard.

In some embodiments, wireless functionality can be provided by standalone 433 MHz ISM devices. In addition, in some embodiments, wireless functionality can be provided modularly, e.g., with a WiFi™ 802.11 ac solution (e.g., add-in card that is backward compatible with IEEE 802.11abgn) with support for Windows 8 CS. This card can be configured in an internal slot (e.g., via an NGFF adapter). An additional module may provide for Bluetooth® capability (e.g., Bluetooth® 4.0 with backwards compatibility) as well as Intel® Wireless Display functionality. In addition, NFC support may be provided via a separate device or multi-function device, and can be positioned as an example, in a front right portion of the chassis for easy access. A still additional module may be a WWAN device that can provide support for 3G/4G/LTE and GPS. This module can be implemented in an internal (e.g., NGFF) slot. Integrated antenna support can be provided for WiFi™, Bluetooth®, WWAN, NFC and GPS, enabling seamless transition from WiFi™ to WWAN radios, wireless gigabit (WiGig) in accordance with the Wireless Gigabit Specification (July 2010), and vice versa.

As described above, an integrated camera can be incorporated into the computing device 500. As one example, this camera can be a high resolution camera, e.g., having a resolution of at least 2.0 megapixels (MP) and extending to 6.0 MP and beyond.

To provide for audio inputs and outputs, an audio processor can be implemented via a digital signal processor (DSP) 556, which may couple to the processor 502 via a high definition audio (HDA) link. Similarly, DSP 556 may communicate with an integrated coder/decoder (CODEC) and amplifier 558 that in turn may couple to output speakers 560, which may be implemented within the chassis. Similarly, the CODEC and amplifier 558 can be coupled to receive audio inputs from a microphone 562, which in an embodiment can be implemented via dual array microphones (such as a digital microphone array) to provide for high quality audio inputs to enable voice-activated control of various operations within the computing device 500. Note also that audio outputs can be provided from the CODEC and amplifier 558 to a headphone jack 564. Although shown with these particular components in the embodiment of FIG. 5, understand the scope of the present techniques is not limited in this regard.

In a particular embodiment, the digital audio codec and amplifier are capable of driving the stereo headphone jack, stereo microphone jack, an internal microphone array, and stereo speakers. In different implementations, the codec can be integrated into an audio DSP or coupled via an HD audio path to a peripheral controller hub (PCH). In some implementations, in addition to integrated stereo speakers, one or more bass speakers can be provided, and the speaker solution can support DTS audio.

In some embodiments, the processor 502 may be powered by an external voltage regulator (VR) and multiple internal voltage regulators that are integrated inside the processor die, referred to as fully integrated voltage regulators (FIVRs). The use of multiple FIVRs in the processor enables the grouping of components into separate power planes, such that power is regulated and supplied by the FIVR to only those components in the group. During power management, a given power plane of one FIVR may be powered down or off when the processor is placed into a certain low power state, while another power plane of another FIVR remains active, or fully powered.

In one embodiment, a sustain power plane can be used during some deep sleep states to power on the I/O pins for several I/O signals, such as the interface between the processor 502 and a PCH, the interface with the external VR and the interface with EC 532. This sustain power plane also powers an on-die voltage regulator that supports the onboard SRAM or other cache memory in which the processor context is stored during the sleep state. The sustain power plane is also used to power on the processor's wakeup logic that monitors and processes the various wakeup source signals.

During power management, while other power planes are powered down or off when the processor 502 enters certain deep sleep states, the sustain power plane remains powered on to support the above-referenced components. However, this can lead to unnecessary power consumption or dissipation when those components are not needed. To this end, embodiments may provide a connected standby sleep state to maintain processor context using a dedicated power plane. In one embodiment, the connected standby sleep state facilitates processor wakeup using resources of a PCH which itself may be present in a package with the processor. In one embodiment, the connected standby sleep state facilitates sustaining processor architectural functions in the PCH until processor wakeup, this enabling turning off all of the unnecessary processor components that were previously left powered on during deep sleep states, including turning off all of the clocks. In one embodiment, the PCH contains a time stamp counter (TSC) and connected standby logic for controlling the computing device 500 during the connected standby state. The integrated voltage regulator for the sustain power plane may reside on the PCH as well.

In an embodiment, during the connected standby state, an integrated voltage regulator may function as a dedicated power plane that remains powered on to support the dedicated cache memory in which the processor context is stored such as critical state variables when the processor enters the deep sleep states and connected standby state. This critical state may include state variables associated with the architectural, micro-architectural, debug state, or similar state variables associated with the processor.

The wakeup source signals from EC 532 may be sent to the PCH instead of the processor during the connected standby state so that the PCH can manage the wakeup processing instead of the processor. In addition, the TSC is maintained in the PCH to facilitate sustaining processor architectural functions. Although shown with these particular components in the embodiment of FIG. 5, understand the scope of the present techniques is not limited in this regard.

Power control in the processor 502 can lead to enhanced power savings. For example, power can be dynamically allocate between cores, individual cores can change frequency/voltage, and multiple deep low power states can be provided to enable very low power consumption. In addition, dynamic control of the cores or independent core portions can provide for reduced power consumption by powering off components when they are not being used.

Some implementations may provide a specific power management IC (PMIC) to control platform power. Using this solution, the computing device 500 may see very low (e.g., less than 5%) battery degradation over an extended duration (e.g., 16 hours) when in a given standby state, such as when in a Win8 Connected Standby state. In a Win8 idle state a battery life exceeding, e.g., 9 hours may be realized (e.g., at 150 nits). As to video playback, a long battery life can be realized, e.g., full HD video playback can occur for a minimum of 6 hours. A platform in one implementation may have an energy capacity of, e.g., 35 watt hours (Whr) for a Win8 CS using an SSD and (e.g.,) 40-44 Whr for Win8 CS using an HDD with a RST cache configuration.

A particular implementation may provide support for 15 W nominal CPU thermal design power (TDP), with a configurable CPU TDP of up to approximately 25 W TDP design point. The platform may include minimal vents owing to the thermal features described above. In addition, the platform is pillow-friendly (in that no hot air is blowing at the user). Different maximum temperature points can be realized depending on the chassis material. In one implementation of a plastic chassis (at least having to lid or base portion of plastic), the maximum operating temperature can be 52 degrees Celsius (C). In addition, for an implementation of a metal chassis, the maximum operating temperature can be 46° C.

In different implementations, a security module such as a TPM can be integrated into the processor 502 or can be a discrete device such as a TPM 2.0 device. With an integrated security module, also referred to as Platform Trust Technology (PTT), BIOS/firmware can be enabled to expose certain hardware features for certain security features, including secure instructions, secure boot, Intel® Anti-Theft Technology, Intel® Identity Protection Technology, Intel® Trusted Execution Technology (TXT), and Intel® Manageability Engine Technology along with secure user interfaces such as a secure keyboard and display.

The block diagram of FIG. 5 is not intended to indicate that the computing device 500 is to include all of the components shown in FIG. 5. Further, the computing device 500 may include any number of additional components not shown in FIG. 5, depending on the details of the specific implementation.

Figure 6:
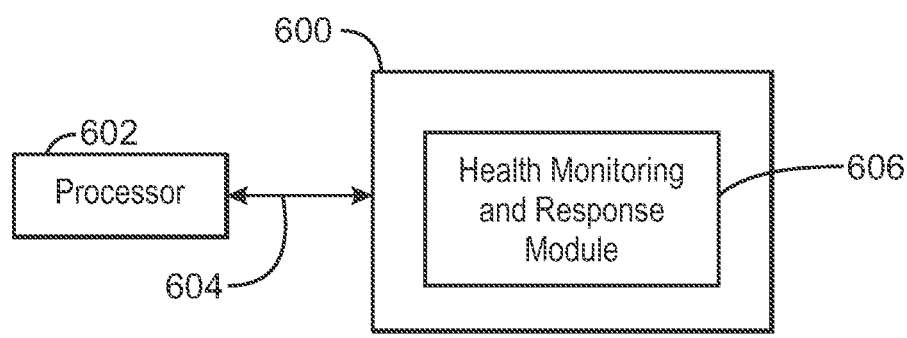
FIG. 6 is a block diagram of a machine-readable medium configured to sense and respond to particular health conditions according to embodiments described herein.

FIG. 6 is a block diagram of a machine-readable medium 600 configured to sense and respond to particular health conditions according to embodiments described herein. The machine-readable medium 600 may be accessed by a processor 602 over a computer bus 604. In various embodiments, the machine-readable medium 600 is a tangible, non-transitory, machine-readable medium. In addition, in some embodiments, the machine-readable medium 600 is a storage medium, but not including carrier waves, signals, and the like. Furthermore, the machine-readable medium 600 may include machine-executable instructions to direct the processor 602 to perform the current method.

The various software components discussed herein may be stored on the machine-readable medium 600, as indicated in FIG. 6. For example, a health monitoring and response module 606 may be configured to detect health conditions corresponding to a user and perform one or more appropriate actions in response to the detected health conditions. In some embodiments, the health monitoring and response module 606 encompasses a number of different modules for performing various tasks, such as analyzing sensor data, testing for certain health conditions, and performing particular actions depending on the detected health conditions. For example, the health monitoring and response module 606 may include one or more modules for controlling certain features of the user's smart home, one or more modules for sending data to other devices or a cloud server, or one or more modules for placing phone calls to the user's emergency contacts or an emergency dispatch center. Further, in some embodiments, the health monitoring and response module 606 may be the same as the health monitoring and response application 508 residing within the mass storage 506 of the computing device 500.

The block diagram of FIG. 6 is not intended to indicate that the machine-readable medium 600 is to include all of the components shown in FIG. 6. Further, the machine-readable medium 600 may include any number of additional components not shown in FIG. 6, depending on the details of the specific implementation.

Examples may include subject matter such as systems and methods that provide a sense-and-act device for health monitoring and response. The sense-and-act device is a wearable device that is configured to sense health conditions corresponding to a user and respond to such health conditions by performing any of a variety of different actions, according to embodiments and examples described herein.

Example 1 includes a wearable computing device for health monitoring and response. The wearable computing device includes a processor, a number of sensors configured to collect data corresponding to a user of the wearable computing device, and a health monitoring and response application, at least partially including hardware logic. The hardware logic of the health monitoring and response application is to test the data collected by any of the number of sensors to match the collected data with a predetermined health condition, determine a current health condition of the user based on the predetermined health condition that matches the collected data, and automatically perform an action based on the current health condition of the user, wherein the action comprises an environmental change.

Example 2 incorporates the subject matter of Example 1. In this example, the sensors include a heart rate sensor, an accelerometer, a gyroscope, a thermal sensor, a galvanic skin response (GSR) sensor, and an electrocardiogram (ECG) sensor, or any combinations thereof.

Example 3 incorporates the subject matter of any combination of Examples 1-2. In this example, the predetermined health condition includes a normal condition, an active condition, a fallen condition, an abnormal heart rate condition, a high blood pressure condition, a fever condition, an allergic reaction condition, a seizure condition, a stroke condition, a heart attack condition, and an abnormal blood sugar level condition, or any combinations thereof.

Example 4 incorporates the subject matter of any combination of Examples 1-3. In this example, the health monitoring and response application automatically sends the collected data and/or information corresponding to the current health condition of the user to a remote computing device via a network.

Example 5 incorporates the subject matter of any combination of Examples 1-4. In this example, the health monitoring and response application automatically sends the collected data and/or information corresponding to the current health condition of the user to a cloud server via a network.

Example 6 incorporates the subject matter of any combination of Examples 1-5. In this example, the action performed by the health monitoring and response application includes automatically controlling one or more features of a home of the user.

Example 7 incorporates the subject matter of any combination of Examples 1-6. In this example, the action performed by the health monitoring and response application includes automatically placing a telephone call to an emergency dispatch center and/or one or more emergency contacts.

Example 8 incorporates the subject matter of any combination of Examples 1-7. In this example, the health monitoring and response application raises an alarm on the wearable computing device and waiting a predetermined amount of time for the user to press an override button before performing one or more other actions.

Example 9 incorporates the subject matter of any combination of Examples 1-8. In this example, the hardware logic of the health monitoring and response application is to prompt the user to complete a general set up procedure prior to first use.

Example 10 incorporates the subject matter of any combination of Examples 1-9. In this example, the wearable computing device is enclosed in a band to be worn around a waist, arm, or leg of the user.

Example 11 incorporates the subject matter of any combination of Examples 1-10. In this example, the wearable computing device is configured to receive, via a network, feedback remotely entered into a web interface, and adjust one or more settings of the wearable computing device based on the feedback.

Example 12 includes an apparatus, including a processor, a number of sensors configured to collect data corresponding to a user of the apparatus, and a health monitoring and response application, at least partially including hardware logic. The hardware logic of the health monitoring and response application is to test the data collected by any of the number of sensors to match the collected data with one or more predetermined health conditions, determine a current health condition of the user based on the predetermined health condition that matches the collected data, and automatically perform one or more actions based on the current health condition of the user.

Example 13 incorporates the subject matter of Example 12. In this example, the number of sensors includes a heart rate sensor, an accelerometer, a gyroscope, a thermal sensor, a galvanic skin response (GSR) sensor, and an electrocardiogram (ECG) sensor, or any combinations thereof.

Example 14 incorporates the subject matter of any combination of Examples 12-13. In this example, the predetermined health condition includes a normal condition, an active condition, a fallen condition, an abnormal heart rate condition, a high blood pressure condition, a fever condition, an allergic reaction condition, a seizure condition, a stroke condition, a heart attack condition, and an abnormal blood sugar level condition, or any combinations thereof.

Example 15 incorporates the subject matter of any combination of Examples 12-14. In this example, the one or more actions performed by the health monitoring and response application includes automatically sending the collected data and/or information corresponding to the current health condition of the user to a remote computing device via a network.

Example 16 incorporates the subject matter of any combination of Examples 12-15. In this example, the health monitoring and response application automatically sends the collected data and/or information corresponding to the current health condition of the user to a cloud server via a network.

Example 17 incorporates the subject matter of any combination of Examples 12-16. In this example, the apparatus is configured to receive, via the network, feedback remotely entered into a web interface, and adjust one or more settings of the apparatus based on the feedback.

Example 18 incorporates the subject matter of any combination of Examples 12-17. In this example, the action performed by the health monitoring and response application includes automatically controlling one or more features of a home of the user.

Example 19 incorporates the subject matter of any combination of Examples 12-18. In this example, the action performed by the health monitoring and response application includes automatically placing a telephone call to an emergency dispatch center and/or one or more emergency contacts.

Example 20 incorporates the subject matter of any combination of Examples 12-19. In this example, the health monitoring and response application raises an alarm on the apparatus and waits a predetermined amount of time for the user to press an override button before performing any other actions.

Example 21 incorporates the subject matter of any combination of Examples 12-20. In this example, the apparatus includes a wearable computing device enclosed in a band to be worn around a waist, arm, or leg of the user.

Example 22 includes a method for sensing and responding to health conditions of a user of a wearable computing device. The method includes collecting, via any of a number of sensors residing within a wearable computing device, data corresponding to a user of the wearable computing device, and testing, via a health monitoring and response application running on the wearable computing device, the collected data to match the collected data with a predetermined health condition. The method also includes determining a current health condition of the user based on the predetermined health condition that matches the collected data, and automatically performing an action based on the current health condition of the user, wherein the action comprises a changing an environmental parameter.

Example 23 incorporates the subject matter of Example 22. In this example, collecting data via any of a number of sensors includes collecting data via a heart rate sensor, an accelerometer, a gyroscope, a thermal sensor, a galvanic skin response (GSR) sensor, and an electrocardiogram (ECG) sensor, or any combinations thereof.

Example 24 incorporates the subject matter of any combination of Examples 22-23. In this example, testing the collected data to match the collected data with the predetermined health condition includes testing the collected data to determine whether the collected data matches a normal condition, an active condition, a fallen condition, an abnormal heart rate condition, a high blood pressure condition, a fever condition, an allergic reaction condition, a seizure condition, a stroke condition, a heart attack condition, or an abnormal blood sugar level condition, or any combinations thereof.

Example 25 incorporates the subject matter of any combination of Examples 22-24. In this example, automatically performing one or more actions based on the current health condition of the user includes automatically sending the collected data and/or information corresponding to the current health condition of the user to a remote computing device via a network.

Example 26 incorporates the subject matter of any combination of Examples 22-25. In this example, automatically performing an action based on the current health condition of the user includes automatically sending the collected data and/or information corresponding to the current health condition of the user to a cloud server via a network.

Example 27 incorporates the subject matter of any combination of Examples 22-26. In this example, automatically performing an action based on the current health condition of the user includes automatically controlling one or more features of a home of the user.

Example 28 incorporates the subject matter of any combination of Examples 22-27. In this example, the method includes automatically performing an action based on the current health condition of the user includes automatically placing a telephone call to an emergency dispatch center and/or an emergency contact.

Example 29 incorporates the subject matter of any combination of Examples 22-28. In this example, automatically performing an action based on the current health condition of the user includes raising an alarm on the wearable computing device and waiting a predetermined amount of time for the user to press an override button before performing another action.

Example 30 incorporates the subject matter of any combination of Examples 22-29. In this example, the method also includes receiving feedback remotely entered into a web interface via a network, and adjusting one or more settings of the wearable computing device based on the feedback.

Example 31 incorporates the subject matter of any combination of Examples 22-30. In this example, automatically performing an action based on the current health condition of the user includes raising an alarm on the wearable computing device, waiting a predetermined amount of time for the user to press an override button, and if the user does not press the override button within the predetermined amount of time, automatically placing a telephone call to an emergency dispatch center and/or one or more emergency contacts.

Example 32 includes a machine readable medium including code that, when executed, causes a machine to perform the method of any combination of examples 22-31.

Example 33 includes an apparatus. The apparatus includes a processor and code to direct the processor to collect, via any of a number of sensors, data corresponding to a user, test the collected data to match the collected data with a predetermined health condition, determine a current health condition of the user based on the predetermined health condition that matches the collected data, and automatically perform an action based on the current health condition of the user.

Example 34 incorporates the subject matter of Example 33. In this example, the action performed by the processor includes automatically controlling one or more features of a home of the user.

Example 35 incorporates the subject matter of any combination of Examples 33-34. In this example, the action performed by the processor includes automatically calling and/or emailing an emergency dispatch center and/or an emergency contact.

Example 36 incorporates the subject matter of any combination of Examples 33-35. In this example, the action performed by the processor includes raising an alarm and waiting a predetermined amount of time for the user to press an override button before performing another action.

Example 37 incorporates the subject matter of any combination of Examples 33-36. In this example, the apparatus includes code to direct the processor to send, via a network, the collected data and/or information relating to the current health condition of the user to a cloud server to be displayed on a web interface. The apparatus also includes code to direct the processor to receive, via the network, feedback remotely entered into the web interface, and adjust a setting of the apparatus based on the feedback.

Example 38 includes computer-readable storage including computer-readable instructions that, when executed, implement a method or realize an apparatus as described in any preceding example.

Example 39 includes tangible, non-transitory, machine-readable medium including code to direct a processor to collect, via any of a number of sensors, data corresponding to a user, and test the collected data to match the collected data with a predetermined health condition. The tangible, non-transitory, machine-readable medium also includes code to direct the processor to determine a current health condition of the user based on the predetermined health condition that matches the collected data, and automatically perform an action based on the current health condition of the user, wherein the action comprises a changing an environmental parameter.

Example 40 incorporates the subject matter of Example 39. In this example, the action performed by the processor includes automatically controlling a feature of a home of the user.

Example 41 incorporates the subject matter of any combination of Examples 39-40. In this example, the action performed by the processor includes automatically calling and/or emailing an emergency dispatch center and/or an emergency contacts.

Example 42 incorporates the subject matter of any combination of Examples 39-41. In this example, the action performed by the processor includes raising an alarm and waiting a predetermined amount of time for the user to press an override button before performing another action.

Example 43 incorporates the subject matter of any combination of Examples 39-42. In this example, the tangible, non-transitory, machine-readable medium includes code to direct the processor to send, via a network, the collected data and/or information relating to the current health condition of the user to a cloud server to be displayed on a web interface. The tangible, non-transitory, machine-readable medium also includes code to direct the processor to receive, via the network, feedback remotely entered into the web interface, and adjust a setting in the tangible, non-transitory, machine-readable medium based on the feedback.

While the present techniques have been described with respect to a limited number of embodiments, those skilled in the art will appreciate numerous modifications and variations therefrom. It is intended that the appended claims cover all such modifications and variations as fall within the true spirit and scope of this present techniques.

A design may go through various stages, from creation to simulation to fabrication. Data representing a design may represent the design in a number of manners. First, as is useful in simulations, the hardware may be represented using a hardware description language or another functional description language. Additionally, a circuit level model with logic and/or transistor gates may be produced at some stages of the design process. Furthermore, most designs, at some stage, reach a level of data representing the physical placement of various devices in the hardware model. In the case where conventional semiconductor fabrication techniques are used, the data representing the hardware model may be the data specifying the presence or absence of various features on different mask layers for masks used to produce the integrated circuit. In any representation of the design, the data may be stored in any form of a machine-readable medium. A memory or a magnetic or optical storage such as a disc may be the machine-readable medium to store information transmitted via optical or electrical wave modulated or otherwise generated to transmit such information. When an electrical carrier wave indicating or carrying the code or design is transmitted, to the extent that copying, buffering, or re-transmission of the electrical signal is performed, a new copy is made. Thus, a communication provider or a network provider may store on a tangible, machine-readable medium, at least temporarily, an article, such as information encoded into a carrier wave, embodying techniques of embodiments of the present techniques.

A "module" as used herein refers to any combination of hardware, software, and/or firmware. As an example, a module includes hardware, such as a micro-controller, associated with a non-transitory medium to store code adapted to be executed by the micro-controller. Therefore, reference to a "module," in one embodiment, refers to the hardware, which is specifically configured to recognize and/or execute the code to be held on a non-transitory medium. Furthermore, in another embodiment, use of a "module" refers to the non-transitory medium including the code, which is specifically adapted to be executed by the microcontroller to perform predetermined operations. And as can be inferred, in yet another embodiment, the term "module" (in this example) may refer to the combination of the microcontroller and the non-transitory medium. Often module boundaries that are illustrated as separate commonly vary and potentially overlap. For example, a first and a second module may share hardware, software, firmware, or a combination thereof, while potentially retaining some independent hardware, software, or firmware. In one embodiment, use of the term "logic" includes hardware, such as transistors, registers, or other hardware, such as programmable logic devices.

Use of the phrase "to" or "configured to," in one embodiment, refers to arranging, putting together, manufacturing, offering to sell, importing and/or designing an apparatus, hardware, logic, or element to perform a designated or determined task. In this example, an apparatus or element thereof that is not operating is still "configured to" perform a designated task if it is designed, coupled, and/or interconnected to perform said designated task. As a purely illustrative example, a logic gate may provide a 0 or a 1 during operation. But a logic gate "configured to" provide an enable signal to a clock does not include every potential logic gate that may provide a 1 or 0. Instead, the logic gate is one coupled in some manner that during operation the 1 or 0 output is to enable the clock. Note once again that use of the term "configured to" does not require operation, but instead focus on the latent state of an apparatus, hardware, and/or element, where in the latent state the apparatus, hardware, and/or element is designed to perform a particular task when the apparatus, hardware, and/or element is operating.

Furthermore, use of the phrases "capable of/to," and or "operable to," in one embodiment, refers to some apparatus, logic, hardware, and/or element designed in such a way to enable use of the apparatus, logic, hardware, and/or element in a specified manner. Note as above that use of "to," "capable of/to," or "operable to," in one embodiment, refers to the latent state of an apparatus, logic, hardware, and/or element, where the apparatus, logic, hardware, and/or element is not operating but is designed in such a manner to enable use of an apparatus in a specified manner.

A "value," as used herein, includes any known representation of a number, a state, a logical state, or a binary logical state. Often, the use of logic levels, logic values, or logical values is also referred to as 1's and 0's, which simply represents binary logic states. For example, a 1 refers to a high logic level and 0 refers to a low logic level. In one embodiment, a storage cell, such as a transistor or flash cell, may be capable of holding a single logical value or multiple logical values. However, other representations of values in computing devices have been used. For example the decimal number ten may also be represented as a binary value of 1010 and a hexadecimal letter A. Therefore, a "value" includes any representation of information capable of being held in a computing device.

Moreover, states may be represented by values or portions of values. As an example, a first value, such as a logical one, may represent a default or initial state, while a second value, such as a logical zero, may represent a non-default state. In addition, the terms reset and set, in one embodiment, refer to a default and an updated value or state, respectively. For example, a default value potentially includes a high logical value, i.e. reset, while an updated value potentially includes a low logical value, i.e. set. Note that any combination of values may be utilized to represent any number of states.

As described with respect to FIG. 6, the embodiments of methods, hardware, software, firmware or code set forth above may be implemented via instructions or code stored on a machine-accessible, machine-readable, computer-accessible, or computer-readable medium which are executable by a processing element. A non-transitory machine-accessible/readable medium includes any mechanism that provides (i.e., stores and/or transmits) information in a form readable by a machine, such as a computer or electronic system. For example, a non-transitory machine-accessible medium includes random-access memory (RAM), such as static RAM (SRAM) or dynamic RAM (DRAM); ROM; magnetic or optical storage medium; flash memory devices; electrical storage devices; optical storage devices; acoustical storage devices; other form of storage devices for holding information received from transitory (propagated) signals (e.g., carrier waves, infrared signals, digital signals), and the like, which are to be distinguished from the non-transitory mediums that may receive information there from.

Instructions used to program logic to perform embodiments of the techniques may be hard coded within circuitry in each of the units described. Further, the logic may be stored within a memory in the system, such as a microcontroller memory, a DRAM, a cache, a flash memory, or other storage. Furthermore, the instructions can be distributed via a network or by way of other computer-readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the computer-readable medium includes any type of tangible machine-readable medium suitable for storing or transmitting electronic instructions or information in a form readable by a machine (e.g., a computer).

Reference throughout this specification to "one embodiment" or "an embodiment" means that a particular feature, structure, or characteristic described in connection with the embodiment is included in at least one embodiment of the present techniques. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

In the foregoing specification, a detailed description has been given with reference to specific exemplary embodiments. It will, however, be evident that various modifications and changes may be made thereto without departing from the broader spirit and scope of the techniques as set forth in the appended claims. The specification and drawings are, accordingly, to be regarded in an illustrative sense rather than a restrictive sense. Furthermore, the foregoing use of "embodiment" and other exemplarily language does not necessarily refer to the same embodiment or the same example, but may refer to different and distinct embodiments, as well as potentially the same embodiment.

What is claimed is:

1. An apparatus for health monitoring and response, comprising:
   a processor;
   a plurality of sensors configured to collect data corresponding to a user of the apparatus; and
   a health monitoring and response application, at least partially comprising hardware logic, wherein the health monitoring and response application is configured to:
      test the data collected by any of the plurality of sensors to match the collected data with one or more predetermined health condition;
      determine one or more current health condition of the user based at least in part on the one or more predetermined health condition that matches the collected data, wherein determining the one or more current health condition of the user includes determining that the user has fallen; and
      automatically perform one or more action based at least in part on the determined one or more current health condition of the user, wherein the one or more action includes in response to determining that the user has fallen, controlling one or more locks.

2. The apparatus of claim 1, wherein the plurality of sensors comprises a heart rate sensor, an accelerometer, a gyroscope, a thermal sensor, a galvanic skin response (GSR) sensor, or an electrocardiogram (ECG) sensor, or any combinations thereof.

3. The apparatus of claim 1, wherein the one or more predetermined health condition comprises a normal condition, an active condition, a fallen condition, an abnormal heart rate condition, a high blood pressure condition, a fever condition, an allergic reaction condition, a seizure condition, a stroke condition, a heart attack condition, or an abnormal blood sugar level condition, or any combinations thereof.

4. The apparatus of claim 1, wherein the health monitoring and response application automatically sends the collected data, or information, or both corresponding to the one or more current health condition of the user to a remote computing device via the network.

5. The apparatus of claim 1, wherein the health monitoring and response application automatically sends the collected data, or information, or both corresponding to the one or more current health condition of the user to a cloud server via the network.

6. The apparatus of claim 1, wherein the one or more action performed by the health monitoring and response application comprises automatically controlling a feature of a home.

7. The apparatus of claim 1, wherein the one or more action performed by the health monitoring and response application comprises automatically placing a telephone call to an emergency dispatch center, or an emergency contact, or both.

8. The apparatus of claim 1, wherein the one or more action performed by the health monitoring and response application comprises raising an alarm on the apparatus and waiting a predetermined amount of time for the user to press an override button before performing other actions.

9. The apparatus of claim 1, wherein the health monitoring and response application is to prompt the user to complete a general set up procedure prior to first use.

10. The apparatus of claim 1, wherein the apparatus is enclosed in a band to be worn around a waist, arm, or leg of the user.

11. The apparatus of claim 1, wherein the one or more action comprises one or more of controlling one or more lights, controlling one or more fans, controlling one or more air conditioners, controlling one or more windows, or controlling one or more features of a vehicle.

12. The apparatus of claim 1, wherein the health monitoring and response application is configured to:
   receive, via a network, feedback based, at least in part, on feedback entered into a web interface available to a remote caregiver; and
   adjust a setting of the apparatus based at least in part on the feedback.

13. The apparatus of claim 1, wherein controlling the one or more locks allows emergency responder access to the user.

14. The apparatus of claim 1, wherein the determining that the user has fallen includes detecting a sudden peak in acceleration followed by a period of no activity.

15. A method for sensing and responding to health conditions of a user of an apparatus, comprising:
   collecting, via any of a plurality of sensors residing within the apparatus, data corresponding to the user of the apparatus;
   testing the collected data via a health monitoring and response application running on the apparatus to match the collected data with one or more predetermined health condition;
   determining one or more current health condition of the user based at least in part on the one or more predetermined health condition that matches the collected data, wherein determining the one or more current health condition of the user includes determining that the user has fallen; and
   automatically performing one or more action based at least in part on the one or more determined current health condition of the user, wherein the one or more action includes in response to determining that the user has fallen, controlling one or more locks.

16. The method of claim 15, wherein collecting data via any of a plurality of sensors comprises collecting data via a heart rate sensor, an accelerometer, a gyroscope, a thermal sensor, a galvanic skin response (GSR) sensor, or an electrocardiogram (ECG) sensor, or any combinations thereof.

17. The method of claim 15, wherein testing the collected data to match the collected data with the one or more predetermined health condition comprises testing the collected data to determine whether the collected data matches a normal condition, an active condition, a fallen condition, an abnormal heart rate condition, a high blood pressure condition, a fever condition, an allergic reaction condition, a seizure condition, a stroke condition, a heart attack condition, or an abnormal blood sugar level condition, or any combinations thereof.

18. The method of claim 15, comprising automatically sending the collected data, or information, or both corresponding to the one or more current health condition of the user to a remote computing device via the network.

19. The method of claim 15, comprising automatically sending the collected data, or information, or both corresponding to the one or more current health condition of the user to a cloud server via the network.

20. The method of claim 15, wherein automatically performing the one or more action comprises automatically controlling a feature of a home.

21. The method of claim 15, wherein automatically performing the one or more action comprises automatically placing a telephone call to an emergency dispatch center, or an emergency contact, or both.

22. The method of claim 15, wherein automatically performing the one or more action comprises raising an alarm on the apparatus and waiting a predetermined amount of time for the user to press an override button before performing another action.

23. The method of claim 15, wherein the one or more action comprises one or more of controlling one or more lights, controlling one or more fans, controlling one or more air conditioners, controlling one or more windows, or controlling one or more features of a vehicle.

24. The method of claim 15, comprising:
receiving, via a network, feedback based, at least in part, on feedback entered into a web interface available to a remote caregiver; and
adjusting a setting of the apparatus based at least in part on the feedback.

25. The method of claim 15, wherein controlling the one or more locks allows emergency responder access to the user.

26. The method of claim 15, wherein the determining that the user has fallen includes detecting a sudden peak in acceleration followed by a period of no activity.

27. A tangible, non-transitory, machine-readable medium comprising code to direct a processor to:
collect, via any of a plurality of sensors, data corresponding to a user;
test the collected data to match the collected data with one or more predetermined health condition;
determine one or more current health condition of the user based at least in part on the one or more predetermined health condition that matches the collected data, wherein determining the one or more current health condition of the user includes determining that the user has fallen; and
automatically perform one or more action based at least in part on the one or more determined current health condition of the user, wherein the one or more action includes in response to determining that the user has fallen, controlling one or more locks.

28. The tangible, non-transitory, machine-readable medium of claim 27, wherein the one or more action performed by the processor comprises automatically controlling a feature of a home.

29. The tangible, non-transitory, machine-readable medium of claim 27, wherein the one or more action performed by the processor comprises automatically calling, or emailing, or both an emergency dispatch center, or an emergency contact, or both.

30. The tangible, non-transitory, machine-readable medium of claim 27, wherein the one or more action performed by the processor comprises raising an alarm and waiting a predetermined amount of time for the user to press an override button before performing another action.

31. The tangible, non-transitory, machine-readable medium of claim 27, wherein the tangible, non-transitory, machine-readable medium comprises code to direct the processor to send, via a network, the collected data, or information, or both relating to the one or more current health condition of the user to a cloud server to be displayed on the web interface.

32. The tangible, non-transitory, machine-readable medium of claim 27, wherein the tangible, non-transitory, machine-readable medium comprises code to direct the processor to:
receive, via a network, feedback based, at least in part, on feedback entered into a web interface available to a remote caregiver; and
adjust a setting in the tangible, non-transitory, machine-readable medium based at least in part on the feedback.

33. The tangible, non-transitory, machine-readable medium of claim 27, wherein the one or more action comprises one or more of controlling one or more lights, controlling one or more fans, controlling one or more air conditioners, controlling one or more windows, or controlling one or more features of a vehicle.

34. The tangible, non-transitory, machine-readable medium of claim 27, wherein controlling the one or more locks allows emergency responder access to the user.

35. The tangible, non-transitory, machine-readable medium of claim 27, wherein the determining that the user has fallen includes detecting a sudden peak in acceleration followed by a period of no activity.

* * * * *